(12) United States Patent
Tsybdenova et al.

(10) Patent No.: US 12,397,085 B2
(45) Date of Patent: Aug. 26, 2025

(54) PRODUCING METHOD OF THE COLLAGEN-LAMININ MATRIX FOR HEALING ULCERS, BURNS AND WOUNDS OF A HUMAN SKIN

(71) Applicant: LIMITED LIABILITY COMPANY "SHENESKIN", Respublika Buryatia (RU)

(72) Inventors: Aryuna Purbodorzhievna Tsybdenova, Orongoy (RU); Erdem Bairovich Dashinimaev, Moscow (RU); Yury Sodnomovich Balkhanov, Respublika Buryatia (RU)

(73) Assignee: LIMITED LIABILITY COMPANY "SHENESKIN", Respublika Buryatia (RU)

(*) Notice: Subject to any disclaimer, the term of this patent is extended or adjusted under 35 U.S.C. 154(b) by 1194 days.

(21) Appl. No.: 17/250,058

(22) PCT Filed: Mar. 20, 2019

(86) PCT No.: PCT/RU2019/050029
§ 371 (c)(1),
(2) Date: Nov. 14, 2020

(87) PCT Pub. No.: WO2019/221639
PCT Pub. Date: Nov. 21, 2019

(65) Prior Publication Data
US 2021/0220518 A1 Jul. 22, 2021

(30) Foreign Application Priority Data
May 15, 2018 (RU) .................. 2018117999

(51) Int. Cl.
| | |
|---|---|
| A61L 27/24 | (2006.01) |
| A61K 35/36 | (2015.01) |
| A61L 27/22 | (2006.01) |
| A61L 27/38 | (2006.01) |
| A61L 27/60 | (2006.01) |
| C12N 5/071 | (2010.01) |

(52) U.S. Cl.
CPC .............. *A61L 27/24* (2013.01); *A61K 35/36* (2013.01); *A61L 27/227* (2013.01); *A61L 27/3813* (2013.01); *A61L 27/60* (2013.01); *C12N 5/0629* (2013.01); *C12N 5/0698* (2013.01); *A61L 2300/412* (2013.01); *A61L 2430/00* (2013.01)

(58) Field of Classification Search
None
See application file for complete search history.

(56) References Cited

U.S. PATENT DOCUMENTS

| | | | |
|---|---|---|---|
| 4,485,096 A | 11/1984 | Bell | |
| 7,338,757 B2* | 3/2008 | Wolfinbarger, Jr. | ......................... A61L 27/3687 435/378 |
| 2001/0044654 A1* | 11/2001 | Chen | ................... A61L 33/0011 600/36 |

OTHER PUBLICATIONS

Translation of Kaporskaya et al, Topical Issues of biomedical engineering. Collection of materials of the VI All-Russian scientific conference for young scientists, 2017. (Year: 2017).*
Gilpin et al, Biomed Res Int, Apr. 2017, vol. 2017, Issue 1, Article ID 9831534. (Year: 2017).*
Shapovalova et al., "Optimization of the collagen carcass type in bioengineering constructions for healing skin ulcers taking into account the embryogenesis of the skin of the human embryos" Vestnik of the Ural Medical Academic Science, 2014, No. 5, pp. 107-110 (4 total pages).
Gould, "Topical Collagen-Based Biomaterials for Chronic Wounds: Rationale and Clinical Application", Advances in wound care (New Rochelle), 2016, vol. 5, No. 1, pp. 19-31 (13 pages).
Meleshina, "Tissue-engineered skin constructs and application of stem cells for creation of skin equivalents (review)", Sovremennye tehnologii v medicine, 2017, vol. 9, No. 1, pp. 198-218 (23 total pages).
Still et al., "The use of a collagen sponge/living cell composite material to treat donor sites in burn patients", Burns, 2003, vol. 29, No. 8, pp. 837-841 (5 pages).
Waymack et al., "The effect of a tissue engineered bilayered living skin analog, over meshed split-thickness autografts on the healing of excised burn wounds", Burns, 2000, vol. 26, No. 7, pp. 609-619 (11 total pages).
International Search Report for PCT/RU2019/050029 dated Aug. 15, 2019, 3 pages.
Akhmedov SH. D. et al. Tkanevaia inzheneriia v eksperimentalnoi serdechno-sosudistoi khirurgii: tekhnologiia polucheniia beskletochnykh kollagenovykh matriksov sosudov zhivotnykh i cheloveka //Kletochnaia transplantologiia i tkanevaia inzheneriia, vol. 6, No. 1, 2011, p. 69-72.
Alekseeva, "Morphological features of the lesion process in the skin under the regional curative effect.—dis. on the joint. d.M.N." 2015, 327 pages (w/ English summary).

(Continued)

*Primary Examiner* — Allison M Fox
(74) *Attorney, Agent, or Firm* — Nixon & Vanderhye PC

(57) ABSTRACT

The proposed invention relates to the medical biotechnologies, to the tissue-derived approaches in regenerative medicine in particular. The method proposes, in addition to conservative treatment methods, substitution therapy for skin damage with the aid of polymer matrices, which are similar to the histotypically of the organism tissues with biologically active agents such as cellular derivatives (collagens and laminins) that contribute to the structural function of the damaged area. A biodegradable wound-healing composite material based on a combination of a polymer substrate and a product of the synthesis of human epithelial cells, devoid of the cell component, is characterized by a relative simplicity of manufacture, the long duration of the storage and can make possible to avoid skin grafting, for example in cases of deep and extensive burns, trophic ulcers, etc.

8 Claims, No Drawings

(56) References Cited

OTHER PUBLICATIONS

Boelsma et al., "Reconstruction of a Human Skin Equivalent Using a Spontaneously Transformed Keratinocyte Cell Line (HaCaT)" *The Journal of Investigative Dermatology*, vol. 112, No. 4: 489-498 (Apr. 1999).

Chandrakasan et al., "Preparation of Intact Monomeric Collagen from Rat Tail Tendon and Skin and the Structure of the Nonhelical Ends in Solution" *The Journal of Biological Chemistry*, vol. 251, No. 19: 6062-6067 (1976).

Frost et al., "Review of the biotechnology market in Russia and assessment of its development prospects, analytical review of the company", 2014, 70 total pages (w/ English summary).

Kaporskaya et al., "Creation of biopolymer matrices for regenerative tissue genesis" Topical issues of biomedical engineering. Collection of materials of the VI All-russian Scientific Conference for Young Scientists.—2017.—p. 39 (w/ English Summary).

Denver M. Faulk et al., "The Effect of Detergents on the Basement Membrane Complex of a Biological Scaffold Material", National Institute of Health (NIH) Public Access, Acta Biomater. Jan. 2014; 10(1):.do:10.1016/j.actbio.2013.09.006, pp. 1-21.

\* cited by examiner

PRODUCING METHOD OF THE COLLAGEN-LAMININ MATRIX FOR HEALING ULCERS, BURNS AND WOUNDS OF A HUMAN SKIN

CROSS-REFERENCE TO RELATED APPLICATIONS

This application is the U.S. national phase of International Application No. PCT/RU2019/050029 filed Mar. 20, 2019 which designated the U.S. and claims priority to RU 2018117999 filed May 15, 2018, the entire contents of each of which are hereby incorporated by reference.

This invention relates to the medical biotechnologies, to the cell technologies and tissue-borne approaches, in particular, developed to solve the problems of regenerative medicine. According to this method substitution therapy is proposed along with conservative treatment methods for healing skin damage with the aid of polymer matrices, which are histotype-similar to body tissues, with biologically active agents: cell derivatives—collagens and laminins that contribute to the structurally forming function of the damaged area.

The use of cell technologies is the most important and rapidly developing field of the modern regenerative medicine. The task of the collagen-laminin matrix is to transplant living cells into the area of the defect and to completely restore the structure and function of the skin, also in stimulating regenerative processes and creating a microenvironment to realize the potential of one's own tissues and cells. Tissue engineering techniques shall be used to solve such problems [8]. Tissue engineering aims to solve many problems of regenerative medicine, which addresses the improvement of the duration and quality of life of an individual by restoring the lost structures and functions of organs and tissues. The use of new materials created on the base of cell technologies can be a forward-looking method of treating and restoring tissues [2, 3, 5, 6].

Approaches based on dermotropic biomedical cell products are currently being developed to treat long-lasting wounds (trophic ulcers, burns) and to restore or temporarily close large areas of skin. The use of cellular technology in stimulating tissue regeneration consists of using cells of different types, biomatrix, and tissue-like structures in different variants and combinations.

There are methods of covering extensive burns with epidermal autografting. However, the use of epidermal layers to treat burn patients meets difficulties with tissue survival rate, in the case of allogenic autografts—with immunogenicity and affordability. Various other types of cells—dermal fibroblasts, mesenchymal bone marrow stem cells, induced pluripotent stem cells—have been successfully used in preclinical and clinical studies. However, this treatment typically requires a large amount of cell material. This is not a major problem in the treatment of small wounds, but it can arise in the treatment of large injuries [8].

There are methods of effective application of dermal components for skin regeneration such as collagen gels, sponges, collagen substrates modified by natural and synthetic polymers, but regenerative processes become complicated by low stability, biocompatibility [9].

Clinical trials with positive results in the closure of relatively small wounds have shown the use of epidermal and dermal skin equivalents consisting of bovine collagen with human neonatal fibroblasts (Apligraf), allogeneic fibroblasts of the foreskin of newborns on a synthetic substrate (Dermagraft), three-dimensional collagen gels with fibroblasts, however, in these variations, difficulties arise with infection, immunogenicity, storage and transportation of tissue-engineered structures. [8, 10].

The claimed method is executed as follows. Type I collagen is obtained from rat tail tendons. This requires adult Wistar line rats (or analogues), weighing 300 grams or more, in laboratory vivarium conditions, excluding infections, parasites, etc. Rat tails after animal euthanization can be cryogenically preserved for several years at −20° C. Prior to the release of collagen, tails are washed with standard detergents and sterilized with 70% ethanol within 24 hours before collagen extraction. All manipulations are then performed under sterile conditions (in laminar cabinets 1 or 2 of the biosafety class). The skin is removed from the tail by means of a scalpel and tweezers, the tail is cut into pieces of 2-3 cm. The resulting tail fragments are further incubated in 70% ethanol for 15 minutes. The tendons are then removed with tweezers from the tail, split into thin fibers and placed in a vessel with a sterile solution of 0.1% ice acetic acid. Collagen begins to be extracted into the solution almost immediately, the solution becomes viscous and colored in blue-opalescent haze type. To obtain the correct concentration and consistency of the solution, the tendons at one tail should be dissolved in 100-150 ml of the solution. The solution is then incubated at +4° C. within a month. If possible, a bottle with a solution should be taken out every day and the residue should be mixed. The result is a thick, viscous liquid with insoluble sediment at the bottom. The collagen solution is then centrifuged (for 1 hour at 1500 g≈4000 rpm with rotor radius 10 cm, at room temperature) to precipitate the unsold collagen fibers. The supernatant is fused into sterile storage tanks. The concentration of the solution can be calculated by evaporating the aqueous fraction in the dry air thermostat and weighing the resulting sediment. A collagen solution can be considered acceptable at a collagen concentration of at least 1 mg/ml (usually 3-5 mg/ml).

For collagen polymerization, the acidic solution of acetic acid should be neutralized. For this purpose, the collagen solution is poured into a sterile petri dish (the dish radius is 3 cm, 6 cm, or 10 cm if necessary) and mixed with a corresponding amount of 0.1M of the NaOH solution to create pH solution ≈7.0-7.2. The solution acidity can be easily determined by adding the M199 formulation containing phenolic red dye, the color of which varies depending on pH. The desired color of the solution is scarlet red. By varying the amount of the collagen solution, it is possible to create matrices of different depths. The polymerization of collagen occurs within 3-5 minutes, so all procedures must be performed quickly, preferably on ice. After adding all the necessary ingredients and mixing, the Petri dish with collagen gel is placed in the incubator at +37° C. for several hours (the day is optimal).

The next day, HaCat line cells are planted on collagen gel at a density of 10000-40000 cells per cm2. HaCat line cells are immortalized human keratinocytes with good proliferation and widely used in scientific research. We top the gel with HaCat cells should up by the necessary amount of the full growth culture medium and the composition is then incubated within a few days before reaching the dense and ultra-dense cell monolayer. During this time, HaCat cells synthesize the laminin layer of the basal membrane on the surface of the gel.

After achieving the required cell density, the resulting matrix is fixed with 4% paraformaldehyde for 1 day at +4° C. Thus, all the proteins of the composition merge together to form an insoluble single complex, the cells become inactivated. After fixation, the transplant is washed away from formaldehyde with a sterile solution of phosphate-salt buffer (PBS), 3 times for 15 minutes swirling in an orbital shaker. Then the matrix goes through the decellularization stage in SDS (sodium dodecyl sulfate) detergent and 0.1% Triton-X-100 (octyl phenyl polyoxyethylene) detergents for 1 day at +4° C. During this process, the bonds between lipids, lipids, and proteins break, and all intracellular components are released and washed out, Degradation of DNA and RNA cells occurs. After decellularization, the transplant is washed away from detergents with a sterile solution of phosphate-salt buffer (PBS), 6 times for 1 hour with swirling on an orbital shaker. The final washing stage is carried out for 1 day at +4° C. The matrix can then be stored for a month at +4° C. in a PBS solution, or two years dried in a cryo freezer at −20° C.

The resulting matrix is a protein composition consisting of two main components, the collagen of the first type, and laminin of the basal membrane, which are in a complete histotypically similarity to the structure of the human skin. Collagen forms a stroma transplant, and laminin covers the stroma in the form of a basal membrane. The matrix is sterile, immunotolerant (since collagen is a highly conserved and immunotolerant protein and laminin has human origin), devoid of any cell component, which makes it a medical product and greatly simplifies the registration procedure.

Various additives (antibiotics, growth factors, cytokines) can be added to the final matrix composition, making it a convenient base model with great development potential. The HaCat cell line can be merged into other immortalized epithelial cell lines producing laminins of other types, allowing the use of the matrix to treat other epithelial-mesenchyme defects (ureter urothelium, laryngeal epithelium, intestinal epithelium, etc.).

The research carried out in vitro with the help of cellular technologies and the application of a biopolymeric substrate made it possible to obtain data on the possibility of forming a stable tissue-engineered histotypes composition on the basis of a collagen matrix extracted in the form of a gel film with a decellularized laminin surface. The immunohistochemical fluorescent analysis identified the expression of composite proteins such as type I collagen and laminin, as well as pan-cytokeratin, a marker of epithelial cells.

The proposed variant of the three-dimensional matrix is a protein composition consisting of two main components, the collagen of the first type, and laminin of the basal membrane, which are in a complete histotypic similarity with the structure of the human skin. Collagen and laminin proteins are the two most common types of human skin protein. Collagen is the basis of the mesenchyme component of the skin dermis, providing its mechanical strength and elasticity. Laminin is the basis of any basal membrane of organs, including the basal membrane of the skin [1, 7].

The results of controlled studies of the dynamics of 21 days simulated on the flap of skin and muscle wound process performed on the Wistar males show that the reduction of the area of wound defects accelerated in 7, 14 days in the groups using the collagen-laminin matrix. The growth of the granulation tissue was observed from the base of the wound, and vascularization was observed in the neoplasms of the connective tissue.

The data obtained on the restoration of the integrity of the skin indicate that the created reparative composition has a high wound healing efficiency, due to the directed growth of regenerating tissue with the maintenance of vascularization processes. The developed biocompatible collagen-laminin wound healing material based on a combination of a polymer substrate and a human keratinocyte synthesis product, while devoid of a cellular component, is characterized by comparative ease of manufacture and a long shelf life, which makes it possible to recommend the design for implementation.

REFERENCES

1. Alekseeva N. T. Morphological features of the lesion process in the skin under the regional curative effect.—dis. on the joint. d.M.N.—2015.—327 p.
2. Grigorian A. S., Kruglyakov P. V. Application in tissue engineering of large transplant vessels based on autogenic mononucleic bone marrow cells/Cellular transplant and tissue engineering.—2009.—Volume IV.—3.—P. 37-41.
3. Kaporskaya A. N., Sinitsyna T. Y., Azizov I. G. Creation of biopolymer matrices for regenerative tissue genesis.—Topical issues of biomedical engineering. Collection of materials of the VI All-russian Scientific Conference for Young Scientists.—2017.—P. 39.
4. Review of the biotechnology market in Russia and assessment of its development prospects, analytical review of the company «Frost&sullivan».—2014.—69 p.
5. Panarin E. F., Nudyga L. A., Petrova V. A., Boček A. M., Hofmann I. V, Lebedeva M. F., Blinova M. I., Spichkina O. G., Yudinseva N. M., Pinaev G. P. Matrices for cultivating human skin cells based on natural polysaccharides-chitin and chitosan/Cellular transplantology and tissue engineering.—2009.—Tom IV.—3.—P. 42-46.
6. Shapovalova E. Y., Boyko T. A., Baranovsky Y. G., Karakulkhina O. A., Baranovsky A. G. Optimization of the collagen carcass type in bioengineering constructions for healing skin ulcers taking into account the embryogenesis of the skin of the human embryos/Vestnik of the Ural Medical Academic Science—2014.—5—P. 107-110.
1. Gould L. J. Topical Collagen-Based Biomaterials for Chronic Wounds: Rationale and Clinical Application./Advances in wound care (New Rochelle).—2016.—Volume 5.—No 1.—P. 19-31.
2. Meleshina A. V., Bystrova A.S., Rogovaya O. S., Vorotelyak E. A., Vasiliev A. V., Zagaynova E. V. Tissue-engineered skin constructs and application of stem cells for creation of skin equivalents (review)./Sovremennye tehnologii v medicine.—2017—9 (1)—P. 198-218.
3. Still J., Glat P., Silverstein P., Griswold J., Mozingo D. The use of a collagen sponge/living cell composite material to treat donor sites in burn patients./Burns.—2003—29 (8)—P. 837-841.
4. Waymack P., Duff R. G., Sabolinski M. The effect of a tissue engineered bilayered living skin analog, over meshed split-thickness autografts on the healing of excised burn wounds. The Apligraf Burn Study Group./Burns.—2000—26 (7)—P. 609-619.

The invention claimed is:

1. A method of producing a tissue-engineered wound composition for healing a human ulcer, burn, or skin wound, the tissue-engineered wound composition comprising a collagen-laminin matrix, the method comprising:
   extracting type I collagen from rat tail tendons;
   providing the extracted type I collagen in the form of a collagen gel film;
   cultivating a monolayer of HaCaT cells on the collagen gel film thereby forming an intermediate matrix;
   fixing the intermediate matrix with 4% paraformaldehyde; and
   removing the HaCaT line cells from the fixed intermediate matrix via a solution of detergents comprising sodium dodecyl sulfate and octyl phenyl polyoxyethylene at a temperature of +4° C. for one day, thereby forming the collagen-laminin matrix that comprises the tissue-engineered wound composition.

2. The method of claim 1, further comprising washing following the removal of the HaCaT line cells.

3. The method of claim 1, wherein the intermediate matrix is fixed using 4% paraformaldehyde at a temperature of +4° C. for one day.

4. The method of claim 1, wherein the collagen-laminin matrix comprises type I collagen and laminin of a basal membrane that histotypically match human skin, the collagen-laminin matrix being sterile, immunotolerant, and devoid of any of the HaCaT line cells.

5. The method of claim 2, further comprising providing an additive to the collagen-laminin matrix.

6. The method of claim 5, wherein the additive is an antibiotics, growth factor, and/or cytokine.

7. The method of claim 2, wherein the HaCat line cells are planted on the collagen gel film at a density of 10000-40000 cells per cm2.

8. The method of claim 2, wherein the HaCaT line is a part of a merged line including one or more other immortalized epithelial cell lines, and the cultivation is performed with the merged line.

* * * * *